(12) United States Patent
Evans et al.

(10) Patent No.: US 11,596,413 B2
(45) Date of Patent: Mar. 7, 2023

(54) METHODS AND SYSTEMS FOR ANEURYSM TREATMENT USING FILLING STRUCTURES

(71) Applicant: Endologix LLC, Irvine, CA (US)

(72) Inventors: Michael A. Evans, Palo Alto, CA (US); Gwendolyn A. Watanabe, Morrisville, NC (US); Amy Lee, Sunnyvale, CA (US); Steven L. Herbowy, Palo Alto, CA (US)

(73) Assignee: Endologix LLC, Irvine, CA (US)

( * ) Notice: Subject to any disclaimer, the term of this patent is extended or adjusted under 35 U.S.C. 154(b) by 0 days.

(21) Appl. No.: 16/900,648

(22) Filed: Jun. 12, 2020

(65) Prior Publication Data

US 2020/0297350 A1    Sep. 24, 2020

Related U.S. Application Data

(60) Continuation of application No. 15/438,682, filed on Feb. 21, 2017, now Pat. No. 10,682,144, which is a
(Continued)

(51) Int. Cl.
*A61B 17/12* (2006.01)
*A61F 2/90* (2013.01)
(Continued)

(52) U.S. Cl.
CPC .. *A61B 17/12118* (2013.01); *A61B 17/12136* (2013.01); *A61F 2/07* (2013.01);
(Continued)

(58) Field of Classification Search
CPC ........ A61B 17/12118; A61B 17/12136; A61B 2017/00893; A61B 2017/1205;
(Continued)

(56) References Cited

U.S. PATENT DOCUMENTS 4,545,367 A * 10/1985 Tucci ............... A61B 17/12109
606/195
4,638,803 A    1/1987 Rand
(Continued)

FOREIGN PATENT DOCUMENTS

EP    1874231    1/2008
EP    1903985    4/2008
(Continued)

OTHER PUBLICATIONS

Final Office Action dated Aug. 23, 2018, from U.S. Appl. No. 15/438,682.
(Continued)

*Primary Examiner* — William H Matthews
(74) *Attorney, Agent, or Firm* — Foley & Lardner LLP

(57) ABSTRACT

Aneurysms are treated by placing a scaffold across an aneurysmal sac to provide a blood flow lumen therethrough. An aneurysmal space surrounding the scaffold is filled with one or more expandable structures which are simultaneously or sequentially expanded to fill the aneurysmal space and reduce the risk of endoluminal leaks and scaffold migration. The expandable structures are typically inflatable and delivered by delivery catheter, optionally with an inflation tube or structure attached to the expandable structure.

22 Claims, 6 Drawing Sheets

Related U.S. Application Data division of application No. 11/444,603, filed on May 31, 2006, now abandoned.

(60) Provisional application No. 60/753,327, filed on Dec. 22, 2005.

(51) Int. Cl.
*A61F 2/954* (2013.01)
*A61F 2/07* (2013.01)
*A61F 2/06* (2013.01)
*A61B 17/00* (2006.01)

(52) U.S. Cl.
CPC ............... *A61F 2/90* (2013.01); *A61F 2/954* (2013.01); *A61B 2017/00893* (2013.01); *A61B 2017/1205* (2013.01); *A61F 2002/065* (2013.01); *A61F 2002/077* (2013.01); *A61F 2230/0078* (2013.01); *A61F 2250/0067* (2013.01)

(58) Field of Classification Search
CPC .... A61F 2/954; A61F 2/90; A61F 2/07; A61F 2250/0067; A61F 2230/0078; A61F 2002/065; A61F 2002/077
See application file for complete search history.

(56) References Cited

U.S. PATENT DOCUMENTS

| | | | |
|---|---|---|---|
| 5,316,023 A | 5/1994 | Palmaz et al. | |
| 5,507,769 A | 4/1996 | Marin et al. | |
| 5,693,088 A | 12/1997 | Lazarus | |
| 5,766,151 A | 6/1998 | Valley et al. | |
| 5,824,054 A | 10/1998 | Khosravi et al. | |
| 5,843,160 A | 12/1998 | Rhodes | |
| 6,428,558 B1 | 8/2002 | Jones et al. | |
| 6,613,074 B1 | 9/2003 | Mitelberg et al. | |
| 6,676,696 B1 | 1/2004 | Marotta | |
| 6,729,356 B1 * | 5/2004 | Baker | D03D 3/08 28/142 |
| 6,730,119 B1 | 5/2004 | Smalling | |
| 2003/0100943 A1 * | 5/2003 | Bolduc | A61B 17/10 623/1.11 |
| 2004/0082989 A1 | 4/2004 | Cook et al. | |
| 2004/0116997 A1 | 6/2004 | Taylor et al. | |
| 2004/0204755 A1 | 10/2004 | Robin | |
| 2005/0004660 A1 | 1/2005 | Rosenbluth et al. | |
| 2005/0020908 A1 | 1/2005 | Birkenbach et al. | |
| 2005/0060017 A1 * | 3/2005 | Fischell | A61B 17/12022 623/1.34 |
| 2005/0149173 A1 | 7/2005 | Hunter et al. | |

FOREIGN PATENT DOCUMENTS

| | | |
|---|---|---|
| FR | 2834199 | 7/2003 |
| WO | 9719653 | 6/1997 |
| WO | 2004045393 | 6/2004 |

OTHER PUBLICATIONS

Final Office Action dated Dec. 7, 2017, from U.S. Appl. No. 15/438,682.
Final Office Action dated Mar. 28, 2019, from U.S. Appl. No. 15/438,682.
Non-final Office Action dated Apr. 5, 2018, from U.S. Appl. No. 15/438,682.
Non-final Office Action dated Jun. 15, 2017, from U.S. Appl. No. 15/438,682.
Non-Final Office Action dated Sep. 18, 2019, from U.S. Appl. No. 15/438,682.
Notice of Allowance dated Feb. 11, 2020, from U.S. Appl. No. 15/438,682.

* cited by examiner

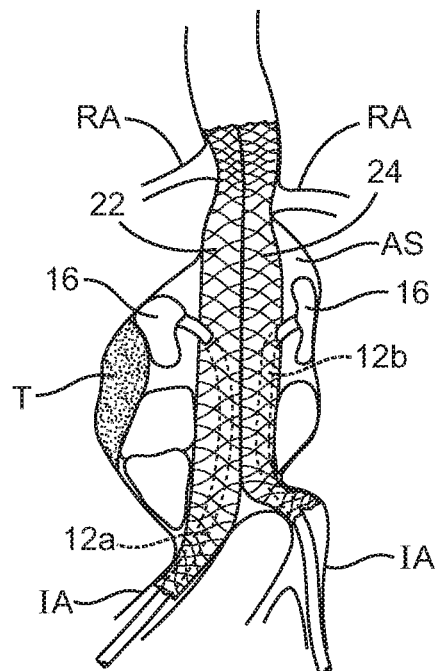
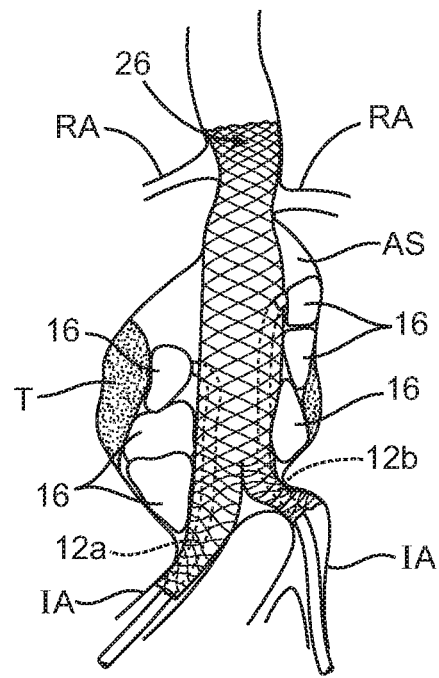
FIG. 6
FIG. 7
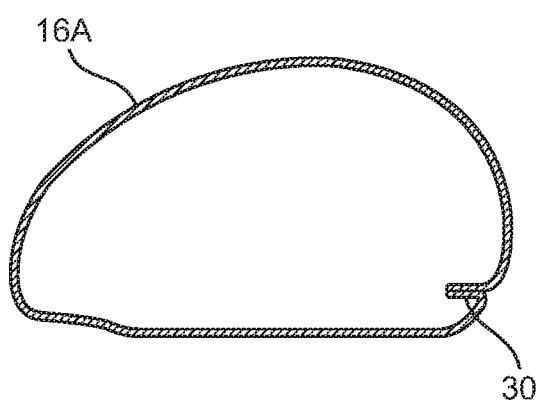
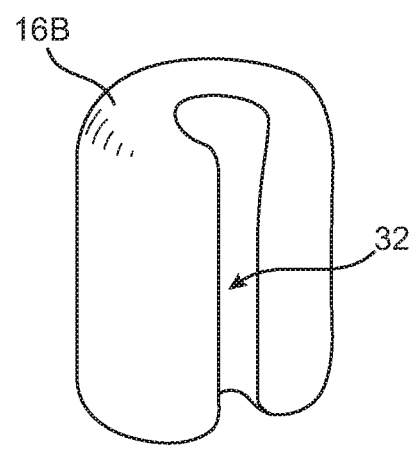
FIG. 8
FIG. 9

METHODS AND SYSTEMS FOR ANEURYSM TREATMENT USING FILLING STRUCTURES

CROSS-REFERENCES TO RELATED APPLICATIONS

This application is a continuation of, and claims benefit and priority of U.S. Non-provisional patent application Ser. No. 15/438,682, filed Feb. 21, 2017, now U.S. Pat. No. 10,682,144, which is a divisional of, and claims benefit and priority of U.S. Non-Provisional patent application Ser. No. 11/444,603, filed May 31, 2006, now Abandoned, which claims benefit and priority of U.S. Provisional Patent Application No. 60/753,327, filed Dec. 22, 2005, the entire contents of each are incorporated herein by reference.

BACKGROUND OF THE INVENTION

1. Field of the Invention

The present invention relates generally to medical apparatus and methods for treatment. More particularly, the present invention relates to methods and systems for crossing and filling abdominal and other aneurysms.

Aneurysms are enlargements or "bulges" in blood vessels which are often prone to rupture and which therefore present a serious risk to the patient. Aneurysms may occur in any blood vessel but are of particular concern when they occur in the cerebral vasculature or the patient's aorta.

The present invention is particularly concerned with aneurysms occurring in the aorta, particularly those referred to as aortic aneurysms. Abdominal aortic aneurysms (AAA's) are classified based on their location within the aorta as well as their shape and complexity. Aneurysms which are found below the renal arteries are referred to as infrarenal abdominal aortic aneurysms. Suprarenal abdominal aortic aneurysms occur above the renal arteries, while thoracic aortic aneurysms (TAA's) occur in the ascending, transverse, or descending part of the upper aorta.

Infrarenal aneurysms are the most common, representing about eighty percent (80%) of all aortic aneurysms. Suprarenal aneurysms are less common, representing about 20% of the aortic aneurysms. Thoracic aortic aneurysms are the least common and often the most difficult to treat. Most or all present endovascular systems are also too large (above 12 F) for percutaneous introduction.

The most common form of aneurysm is "fusiform," where the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. The most common treatment for each of these types and forms of aneurysm is open surgical repair. Open surgical repair is quite successful in patients who are otherwise reasonably healthy and free from significant co-morbidities. Such open surgical procedures are problematic, however, since access to the abdominal and thoracic aortas is difficult to obtain and because the aorta must be clamped off, placing significant strain on the patient's heart.

Over the past decade, endoluminal grafts have come into widespread use for the treatment of aortic aneurysm in patients who cannot undergo open surgical procedures. In general, endoluminal repairs access the aneurysm "endoluminally" through either or both iliac arteries in the groin. The grafts, which typically have been fabric or membrane tubes supported and attached by various stent structures, are then implanted, typically requiring several pieces or modules to be assembled in situ. Successful endoluminal procedures have a much shorter recovery period than open surgical procedures.

Present endoluminal aortic aneurysm repairs, however, suffer from a number of limitations. A significant number of endoluminal repair patients experience leakage at the proximal juncture (attachment point closest to the heart) within two years of the initial repair procedure. While such leaks can often be fixed by further endoluminal procedures, the need to have such follow-up treatments significantly increases cost and is certainly undesirable for the patient. A less common but more serious problem has been graft migration. In instances where the graft migrates or slips from its intended position, open surgical repair is required. This is a particular problem since the patients receiving the endoluminal grafts are often those who are not considered good candidates for open surgery. Further shortcomings of the present endoluminal graft systems relate to both deployment and configuration. Current devices are unsuitable for treating many geometrically complex aneurysms, particularly infrarenal aneurysms with little space between the renal arteries and the upper end of the aneurysm, referred to as short-neck or no-neck aneurysms. Aneurysms having torturous geometries, are also difficult to treat.

For these reasons, it would be desirable to provide improved methods and systems for the endoluminal and minimally invasive treatment of aortic aneurysms. In particular, it would be desirable to provide systems and methods which provide prostheses with minimal or no endoleaks, which resist migration, which are relatively easy to deploy, and which can treat many if not all aneurysmal configurations, including short-neck and no-neck aneurysms as well as those with highly irregular and asymmetric geometries. It would be further desirable to provide systems and methods which are compatible with current designs for endoluminal stents and grafts, including single lumen stents and grafts, bifurcated stents and grafts, parallel stents and grafts, as well as with double-walled filling structures which are the subject of the commonly owned, copending applications described below. The systems and methods would preferably be deployable with the stents and grafts at the time the stents and grafts are initially placed. Additionally, it would be desirable to provide systems and methods for repairing previously implanted aortic stents and grafts, either endoluminally or percutaneously. At least some of these objectives will be met by the inventions described hereinbelow.

2. Description of the Background Art

US2006/0025853 describes a double-walled filling structure for treating aortic and other aneurysms. Copending, commonly owned application Ser. No. 11/413,460, describes the use of liners and extenders to anchor and seal such double-walled filling structures within the aorta. The full disclosures of both these pending applications are incorporated herein by reference. WO 01/21108 describes expandable implants attached to a central graft for filling aortic aneurysms. See also U.S. Pat. Nos. 5,330,528; 5,534,024; 5,843,160; 6,168,592; 6,190,402; 6,312,462; 6,312,463; US2002/0045848; US2003/0014075; US2004/0204755; US2005/0004660; and WO 02/102282.

BRIEF SUMMARY OF THE INVENTION

The present invention provides methods and systems for the treatment of aneurysms, particularly aortic aneurysms including both abdominal aortic aneurysms (AAA's) and thoracic aortic aneurysms (TAA's). Treatments are particularly useful in endoluminal protocols where vascular catheters may be used to advance and manipulate the various system components. In some instances, however, the systems and methods will also be useful for the percutaneous, minimally invasive treatment of aneurysms where the aneurysm may be accessed from the outside through a controlled penetration in the aneurysmal wall.

Systems according to the present invention comprise a scaffold which is adapted to be placed across the aneurysm to provide one or more blood flow lumens thereacross. The scaffold may be any type of conventional aneurysmal treatment scaffold, including bare stents, grafts, stent-reinforced grafts, double-walled filling structures (as described in detail in copending application Ser. No. 11/413,460, the full disclosure of which has been previously incorporated herein by reference), and the like. Optionally, the scaffold will be coated with, impregnated with, or otherwise adapted to carry a medicament which will be released in the aneurysmal sac after the scaffold is implanted therein. The present invention will primarily rely on stents and grafts which are endoluminally placed to provide the desired blood flow lumen(s) across the aneurysm and to define an aneurysmal space between an outside surface of the scaffold and an inside surface of all or a portion of the aneurysmal wall. As discussed above in the Background section, the aneurysmal space which remains around an aneurysmal scaffold is subject to leakage and in some cases allows for migration of the scaffold from the originally implanted location. Both outcomes are undesirable, and the methods and systems of the present invention will help both seal the aneurysmal space in order to reduce the risk of leakage and help anchor the aneurysmal scaffold in place to reduce the risk of migration.

The present invention provides for the deployment of one or more expandable structures, such as inflatable balloons or bladders, within the aneurysmal space. The expandable structures are usually placed after deployment of the aneurysmal scaffold and more usually are deployed through the wall of the scaffold into the aneurysmal space. In other instances, however, the space-filling expandable structures may be deployed prior to placement of the aneurysmal scaffold, where such pre-deployed expandable structures may be expanded either before or after deployment of the aneurysmal scaffold. In other instances, the expandable structures of the present invention may be deployed days, weeks, or even longer after an initial endoluminal or other aneurysmal repair. The expandable structures are useful for developing voids which may open around a previously implanted scaffold over time. For such "revision" treatments, the expandable structures may be placed through the aneurysmal scaffold or may be percutaneously placed through the wall of the aneurysm.

When filling the aneurysmal space after deployment of an aneurysmal scaffold, it is necessary to avoid over pressuring the aneurysmal sac in order to reduce the risk of accidental rupture. The present invention provides different protocols for controlling pressurization within the aneurysmal space as the expandable structure is being expanded. For example, excess expansion medium being fed to one or more of the expandable structures may be selectively bled from the structure if the pressure within the aneurysmal space is excessive. A drain tube or lumen may be connected to the expandable structure while it is being expanded in order to bleed the excess expansion medium. Such selective bleeding could be controlled by a pressure relief valve, a feedback pressure control system, or the like. Alternatively, excessive pressurization within the aneurysmal sac can be controlled by bleeding fluid from the aneurysmal space as the expandable structure is being expanded. Such control could be provided by one or more drain catheters deployed directly into the aneurysmal space and connected to pressure relief valves or active pressure control systems.

In a first aspect of the present invention, methods are provided for treating an aneurysm in a blood vessel by placing a scaffold across the aneurysm to define an aneurysmal space between an outside surface of the scaffold and an inside surface of the aneurysmal wall. At least one expandable structure is expanded using an expansion medium which passes by or through the scaffold or through the aneurysmal wall to fill at least a portion of the aneurysmal space.

The scaffold may comprise any conventional vascular scaffold of a type which may be positioned across an aneurysm. For example, the scaffold could comprise a conventional bare metal stent having sufficient length and suitable diameter to be implanted across the aneurysm with a first end anchored in healthy vasculature on one side of the aneurysm and a second end anchored in healthy vasculature on the other side of the aneurysm. Such bare metal stents may be balloon expandable, self-expanding, provide for a ratcheting expansion, or the like. Alternatively, fabric, braid, or other vascular grafts may be anchored in healthy vasculature on either side of the aneurysm, often using barbs, staples, or the like. The graft structures will typically comprise a blood-impermeable wall, and thus the expandable structures will typically be delivered before graft deployment, around a partially deployed graft, or through the aneurysmal wall, as described generally below. In addition to stents and grafts, the present invention can use stent-reinforced graft structures which are typically expanded and anchored within the target blood vessel. Such stent-grafts may also be balloon expandable, self-expanding, or a combination thereof.

The systems and methods of the present invention may be used to treat aneurysms having a variety of geometries. While the systems and methods are particularly useful for treating aneurysms wherein the enlargement circumscribes the blood vessel (fusiform), such as most aortic aneurysms, they will also be useful for treating various asymmetric aneurysms where the bulge is present over only a portion of the periphery of the blood vessel wall. In all cases, it is generally desirable that the expandable structures occupy at least most and preferably all of the void in the aneurysmal space in order to most effectively inhibit leakage and migration of the scaffold.

The methods and systems of the present invention are compatible with the use of both single scaffolds and multiple scaffold systems. In treating linear aneurysms, two or more stents, grafts, or other scaffolds may be placed in series in order to span the entire length of the aneurysm. In bifurcated aneurysms, such as abdominal aortic aneurysms, a pair of parallel scaffolds may be placed in the aneurysm and extend from the aorta into each of the iliac branch vessels. Alternatively, bifurcated scaffolds having branch ends may be placed from the aorta into the iliac arteries. When treating such branch vessels, it will also be possible to add stents, cuffs, and other sealing members which extend the length of the scaffold at either end.

The expandable structures will typically be balloons or other structures which are inflatable with a fluid inflation medium. Such inflatable structures will typically have a fluid impermeable wall which is sufficiently flexible to conform to the aneurysmal wall, the scaffold, and other expandable structure(s) which may be or have been placed in the aneurysmal space. The inflatable structures may be elastic or non-elastic, typically being formed from parylene, polyester (e.g., Dacron®), PET, PTFE, and/or a compliant material, such as silicone, polyurethane, latex, or combinations thereof. Usually, it will be preferred to form at least a portion of the inflatable member partially or entirely from a non-compliant material to enhance conformance of the outer wall of the scaffold to the inner surface of the aneurysm.

The walls of the expandable structures may consist of a single layer or may comprise multiple layers which are laminated, glued, heat bonded, ultrasonically bonded, or otherwise formed together. Different layers may comprise different materials, including both compliant and/or non-compliant materials. The structure walls may also be reinforced in various ways, including braid reinforcement layers, filament reinforcement layers, and the like.

The expandable structures of the present invention may also be expanded with non-fluid expansion medium, such as powders, pellets, coils, foams, and the like. In such instances, the expandable structure will not necessarily be formed from an impermeable material, but instead could be formed from lattices, braids, nets, or other permeable or foramenous structures which contain the expansion medium but might permit blood and fluid permeation.

In some instances, the expandable structure will be extruded in situ, typically at the same time that it is being expanded or inflated with a separate expansion material. Various extrudable polymers exist which can be delivered from a delivery catheter.

Expanding the expandable structure will usually be performed at least in part using a delivery catheter which both positions and fills the expansion structure within the aneurysmal space. Most commonly, the delivery catheter will be positioned inside of the scaffold and will deliver the expansion medium through the catheter wall. In other instances, however, the delivery catheter may be positioned around one end of the scaffold to permit positioning and filling of the expandable structure before or after the scaffold has been placed. In still further instances, the delivery catheter may be passed through a penetration in the aneurysmal wall to access a void in the aneurysmal space which requires filling.

In a first exemplary embodiment, the delivery catheter will be used to deliver and position the expandable structure through the scaffold wall after the scaffold has been placed in the aneurysm. The delivery catheter may be passed through a discrete window or opening formed in the scaffold wall which is enlarged relative to other openings and intended particularly for delivering the expandable structure. More typically, however, the delivery catheter will be passed through openings or interstices which are inherently part of the cellular construction of the scaffold. By passing through the cellular openings which are already present, multiple expandable structures may be placed at locations which may be determined during the course of the procedure.

In alternative protocols, the delivery catheter may be used to place the expandable structure prior to delivery of the scaffold. The scaffold may then be placed so that at least one end of the scaffold is deployed and anchored over the delivery catheter(s). In such instances, the expandable structures will usually be inflated or otherwise expanded after the scaffold is deployed. Alternatively, the expandable structures may be expanded at least partly prior to deployment of the scaffold so long as care is taken not to over pressurize the aneurysmal sac when the scaffold is expanded and implanted.

In yet another protocol, the delivery catheter may be introduced into the aneurysmal space by passing a cannula or other delivery tube through a penetration in the aneurysmal wall. The cannula may be positioned using thoracoscopic or other minimally invasive techniques in order to access the outside wall of the aneurysm. Such percutaneous deployment of the expandable structures will be particularly suitable for treating patients where a void or expansion of the aneurysmal sac has occurred sometime after a primary treatment.

Usually, at least two expandable structures will be delivered to substantially fill the aneurysmal space. Often, three, four, five, or even more expandable structures may be delivered. Typically, the treating physician will sequentially deliver multiple expandable structures through the wall of the aneurysmal scaffold while visualizing the aneurysmal space fluoroscopically. A sufficient number of expansion members can then be delivered in order to substantially fill the void within the aneurysmal space, as confirmed by the fluoroscopic visualization. In other instances, two or more expandable structures may be expanded simultaneously, in mixed protocols where expandable structures are sometimes delivered simultaneously and other times delivered sequentially may also be employed.

In a second aspect of the present invention, systems for treating an aneurysm in a blood vessel comprise a scaffold, and expandable structure, and a delivery catheter. The scaffold may comprise any of the scaffolds generally described above in connection with the methods of the present invention. The delivery catheters will typically comprise a flexible elongate tubular member having at least one lumen therethrough for delivering expansion medium to the expandable structure. In some embodiments, the expandable structure may be initially attached at a distal end of a delivery catheter and the lumen of the delivery catheter used only for delivering the expansion medium to the expandable structure. The expandable structure will be detachable from the delivery catheter after it has been filled and will usually include a self-sealing valve or other attachment port which closes and retains the expansion medium within the structure after detachment of the delivery catheter. In other instances, the delivery catheter may be adapted to deliver both the expandable structure and the expansion medium to the expandable structure. In such instances, the delivery catheter can be used for sequentially delivering two or more expansion structures together with filling of those structures. In still other instances, separate delivery catheters or delivery catheter components may be used for delivering an expandable structure and for filling the expandable structure.

The systems of the present invention may further comprise a cannula for positioning a delivery catheter and expandable structure percutaneously through the wall of an aneurysm. The cannula will have an axial lumen for containing the expandable structure and/or delivery catheter can be used to access the aneurysm in a conventional manner.

BRIEF DESCRIPTION OF THE DRAWINGS

FIG. 6 illustrates the use of a pair of delivery catheters for delivering expandable structures through separate parallel scaffolds.

FIG. 7 illustrates the use of a pair of delivery catheters for delivering multiple expandable structures through a single bifurcated scaffold.

FIG. 8 illustrates positioning of a valve in an exemplary expandable structure in accordance with the principles of the present invention.

FIG. 9 illustrates and expandable structure having an axial channel or groove for receiving a deployed scaffold in accordance with the principles of the present invention.

DETAILED DESCRIPTION OF THE INVENTION

Figure 1:
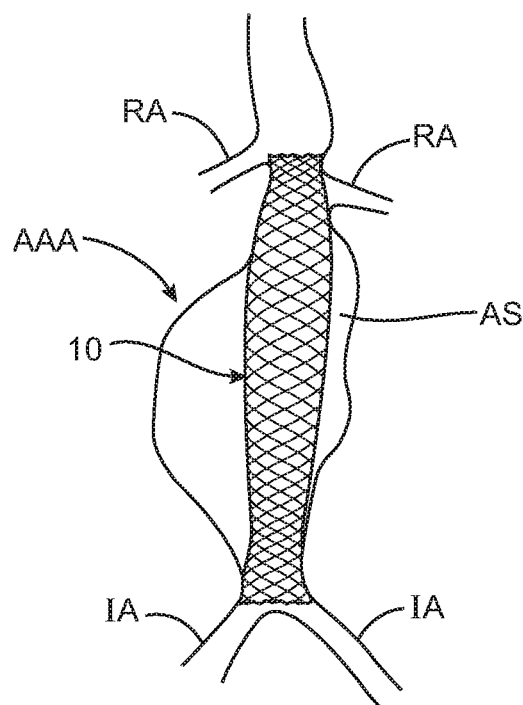
FIG. 1 illustrates a single scaffold placed across an abdominal aortic aneurysm and creating an aneurysmal space around the scaffold.

Referring to FIG. 1, in accordance with the principles of the present invention a scaffold 10 is placed within an aneurysm to span the length of the aneurysm between regions of relatively healthy vasculature. Scaffold 10 is illustrated in an abdominal aortic aneurysm AAA and extends from the renal arteries RA to the iliac arteries IA. The scaffold 10 is shown as a bare metal stent which may be balloon expandable or self-expanding within the aneurysm. It will be appreciated, that the scaffold could comprise a more conventional graft structure, a stent-graft structure, and could comprise barbs, hooks, staples, or other elements for anchoring the scaffold within the regions of healthy vasculature. As shown in FIG. 1, an annular aneurysmal space AS circumferentially surrounds the scaffold 10. The method and systems of the present invention are intended for at least partially and preferably substantially completely filling the aneurysmal space to reduce the risk of endoleaks and to anchor the scaffold to inhibit migration.

Figures 2A, 2B:
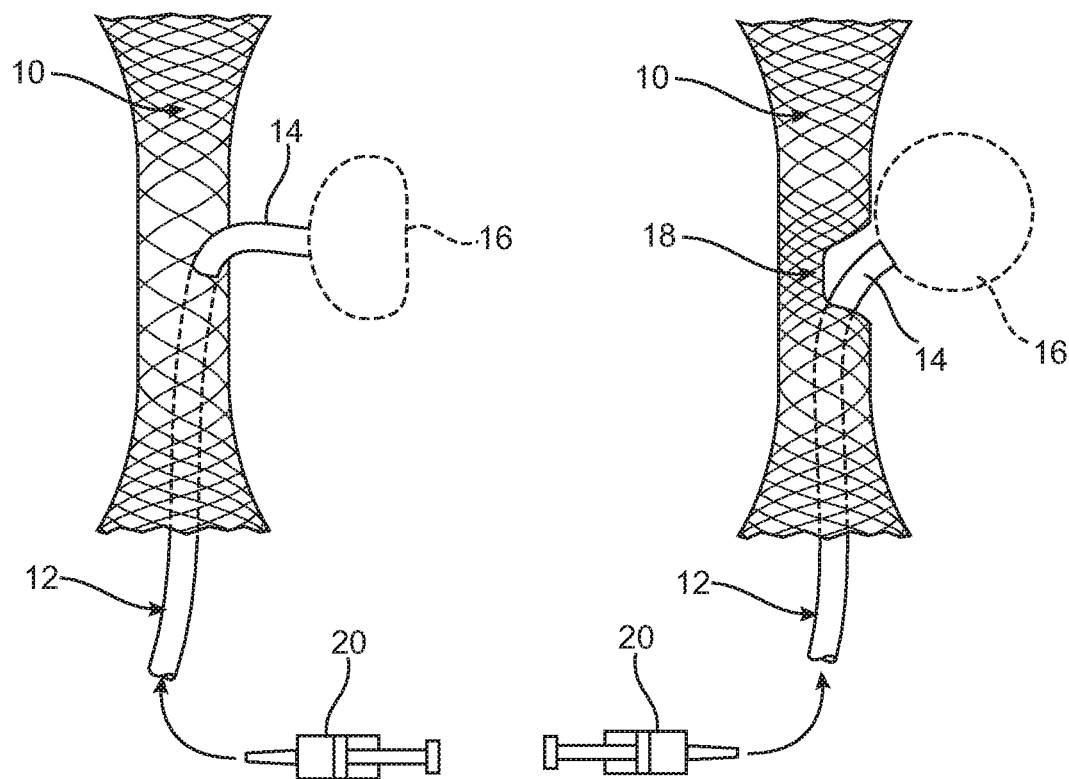
FIGS. 2A and 2B illustrate use of a delivery catheter in accordance with the principles of the present invention for positioning and expanding an expandable structure in accordance with the principles of the present invention.

Referring now to FIGS. 2A and 2B, delivery catheters 12 may be used to both deliver expandable structures 16 and to fill the expandable structures with an expansion medium, for example by using a syringe 20 to deliver the medium through a lumen of the catheter 12. Most commonly, the distal end 14 of the delivery catheter 12 will be positioned through openings in the cellular structure of the scaffold 10, as shown in FIG. 2A. Alternatively, as shown in FIG. 2B, a window 18 may be formed within a wall of the scaffold 10 to permit positioning of the distal end 14 of the delivery catheter 12 therethrough. Use of such a window will usually be compatible only with the delivery of single expandable structure 16 which can occupy substantially the entire aneurysmal space AS. Thus, delivery through the normal opening in the cellular structure of a stent or other scaffold 10 will normally be preferred since it allows the physician to deliver and position multiple expandable structures 16 as needed in order to fully occupy the void region of the aneurysmal space AS.

Figure 3:
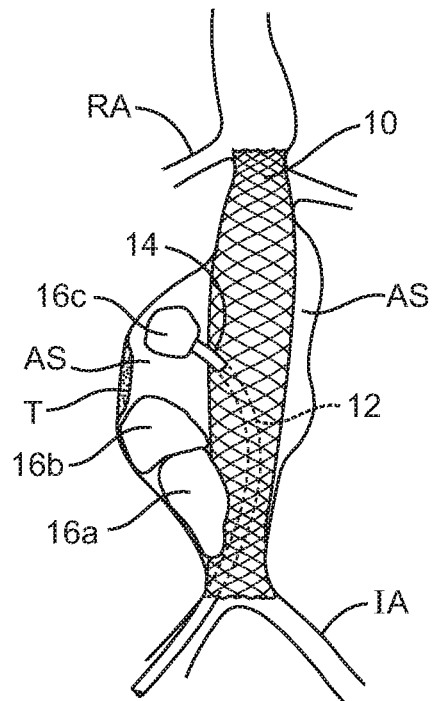
FIGS. 3 and 4 illustrate use of a single delivery catheter for delivering multiple expandable structures in accordance with the principles of the present invention.

Use of a single delivery catheter 12 for sequentially positioning a plurality of expandable structures 16a-16c is illustrated in FIG. 3. A catheter 12 is used to deliver a first expandable structure 16a, moved and extended out through a different portion of the scaffold 10, and then used to deliver a second expandable structure 16b. A third expandable structure 16c is shown as being inflated and delivered in FIG. 3. When using a single delivery catheter 12 to deliver multiple expandable structure 16, it will usually be desirable to employ separate inflatable members with inflation tubes detachably fixed thereto. Thus, the inflatable expansion member 16 can be delivered, inflated with the inflation tube, and then detached and left in place. After withdrawing one inflation tube, a second inflation tube can then be used to deliver a second inflatable expandable structure 16. Positioning of the expandable structure 16 can be effected by repositioning the delivery catheter 12 and/or extending the inflatable tube (not shown) from the delivery catheter 12 into different regions of the aneurysmal space AS as needed to fill different portions of the space.

Figure 4:
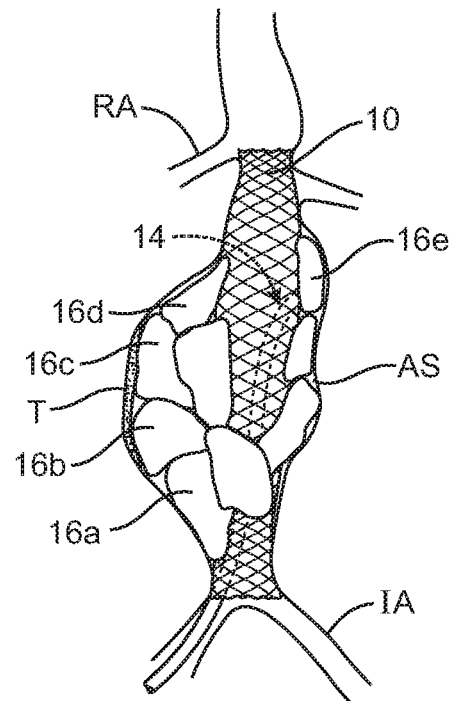

Referring now to FIG. 4, the catheter 12 of FIG. 3 has been used to deliver additional expandable structures 16, with a fourth and a fifth expandable structure 16d and 16e shown as being deployed. Additional expandable structures 16 will be added until the entire aneurysmal space AS is filled, usually as confirmed under fluoroscopic. A single catheter 12 has been introduced to the aneurysmal space AS through the iliac artery IA.

Figure 5:
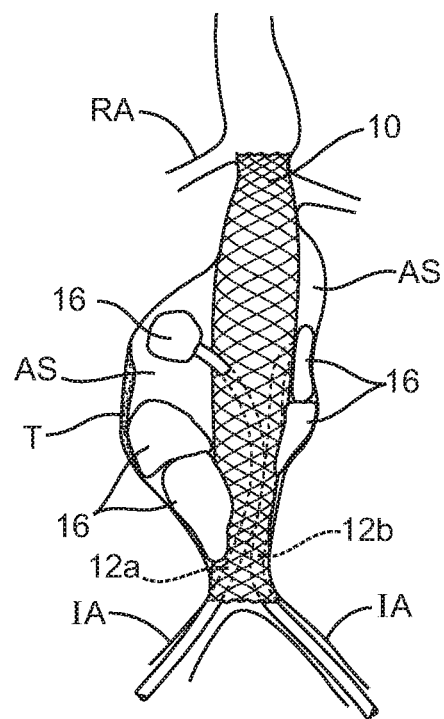
FIG. 5 illustrates the use of a pair of delivery catheters for delivering multiple expandable structures in accordance with the principles of the present invention.

Referring now to FIG. 5, a pair of delivery catheters 12a and 12b can be used to simultaneously position two expandable structures 16. The delivery catheters 12a and 12b are introduced through the two iliac arteries IA, and they may be used to both simultaneously and sequentially deliver multiple expandable structures 16.

Referring now to FIG. 6, a pair of delivery catheters 12a and 12b can be used simultaneously and/or sequentially deliver multiple expandable structures 16 through a pair of parallel scaffold 22 and 24. The upper ends of the scaffolds 22 and 24 are positioned in the aorta and anchored above the renal arteries RA, while the lower ends are respectively in the right and left iliac arteries IA. The delivery catheters are introduced through the iliac arteries into the lower ends of the scaffolds 22 and 24. Similarly, a pair of delivery catheters 12a and 12b can be used to deliver multiple expandable structures 16 simultaneously or sequentially through a bifurcated lower end of a bifurcated stent 26, as shown in FIG. 7. In all the cases described thus far, the multiple expandable structures 16 are particularly adapted to conform around regions of thrombus T within the aneurysmal space AS.

The expandable structure 16 can take a variety of forms. As shown in FIG. 8, expandable structure 16A comprises an outer wall formed from a flexible material, typically a polymer as described above. A valve structure 30 is provided to detachably secure to the distal end of a delivery catheter or inflation tube. The delivery catheter tube may deliver any one of the expandable media described above, and the valve 30 will usually be self-closing after the delivery catheter inflation tube is detached. As shown in FIG. 9, and expandable structure 16B can be shaped from semi-compliant or non-compliant materials to provide a particular filling geometry. The expandable structure 16B has a C-shaped cross-section which is particularly useful for filling an annular aneurysmal space surrounding a scaffold where the scaffold is received in an axial channel 32 in the expandable structure.

Figure 10A:
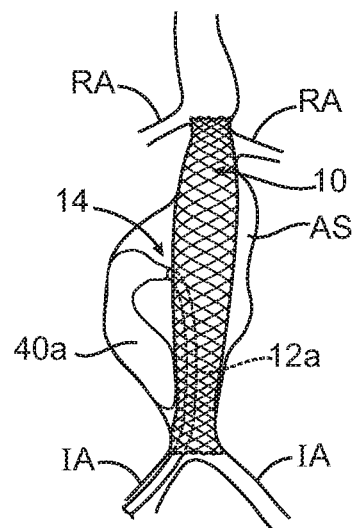
FIGS. 10A-10E illustrate use of a delivery catheter for extruding pairs of expandable structures in accordance with the principles of the invention.
Figure 10B:
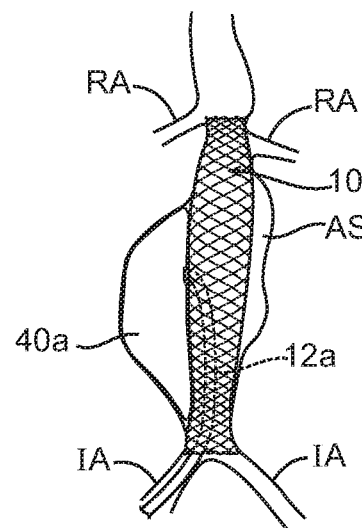
Figure 10C:
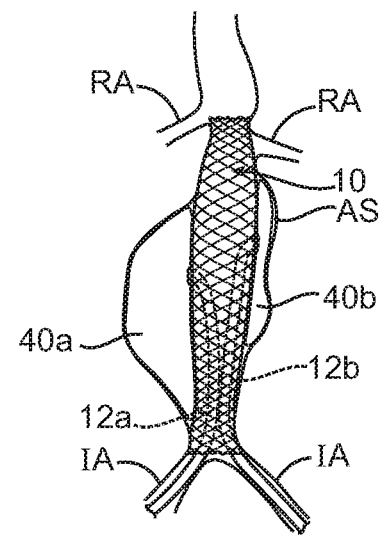
Figure 10D:
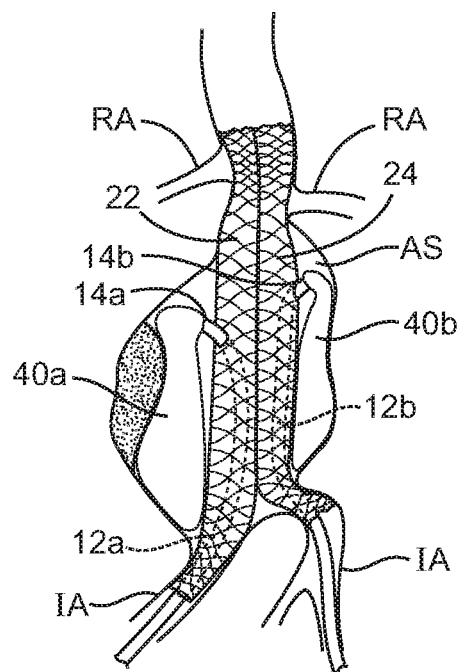
Figure 10E:
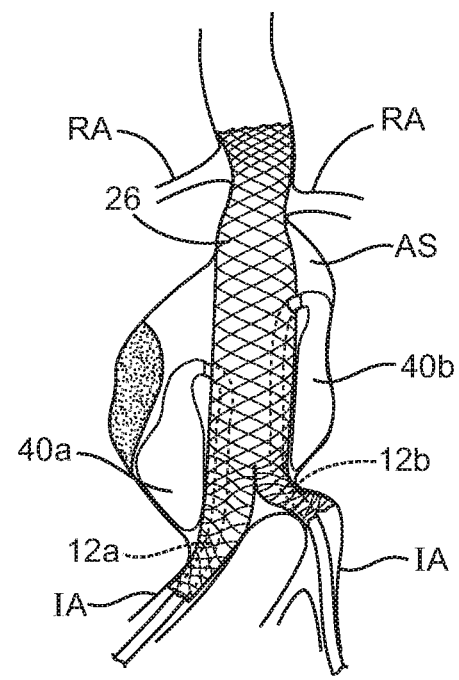

Referring now to FIGS. 10A to 10E, expandable structures 40 may be extruded around the scaffold 10. A highly conformable bag may be pushed out from the delivery catheter 12 under pressure from the fill material. As shown in FIG. 10A, a first extrudable expandable structure 40a is delivered by a first delivery catheter 12a, so that it expands and conforms to the scaffold 10, as shown in FIG. 10B. Optionally, a second extrudable expandable structure 40b may be delivered using a second delivery catheter 12b, as shown in FIG. 10C. The delivery of extrudable expandable structures may similarly be performed in parallel stents 22 and 24, as shown in FIG. 10D or in bifurcated stents 26 as shown in FIG. 10E. Once the aneurysmal space AS has been substantially filled, the extrudable expandable structures 40 may be sealed, optionally with a heating element, a clip, an adhesive, or other techniques for terminating the extrusion. The delivery catheters can then be removed, leaving the extruded expandable structures in place.

Figure 11A:
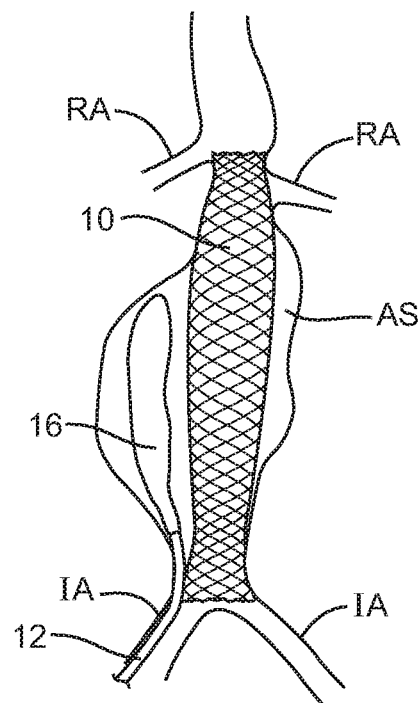
FIGS. 11A-11D illustrate delivery of expandable structures where the delivery catheter is placed past one end of a scaffold in accordance with the principles of the present invention.
Figure 11B:
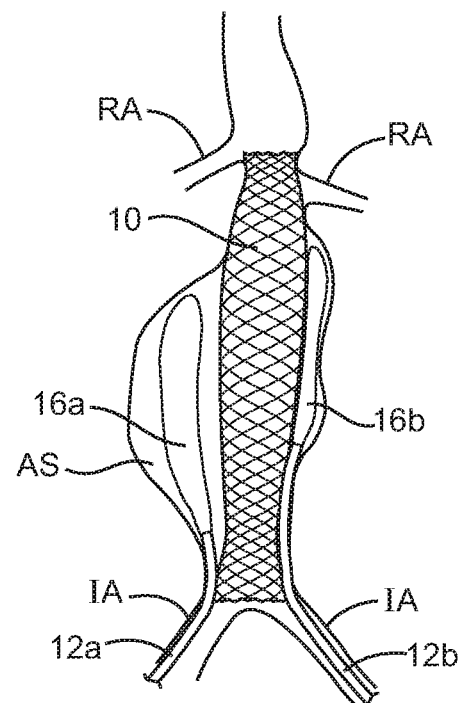
Figure 11C:
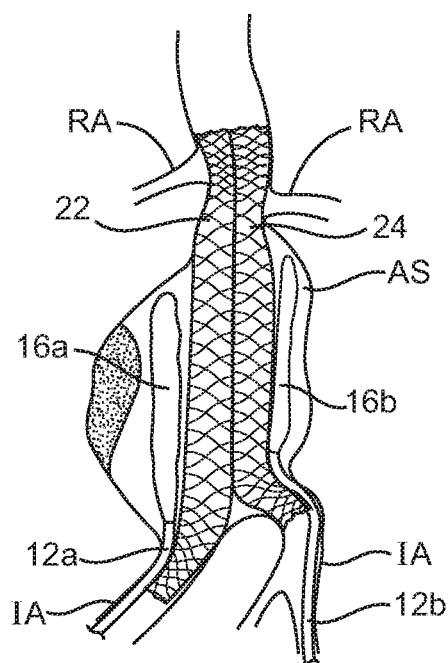
Figure 11D:
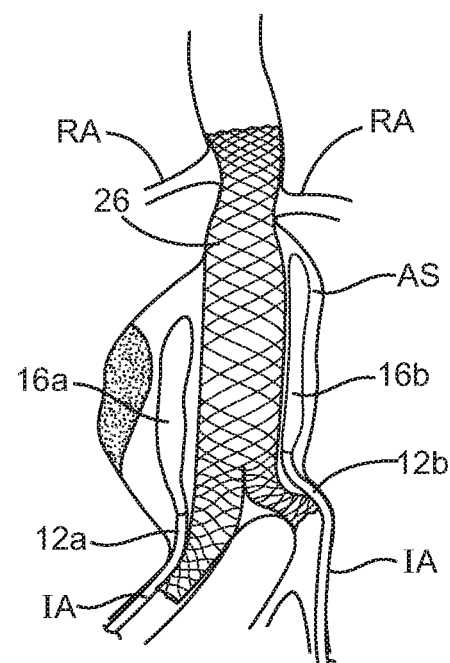

As described thus far, the expandable structures 16 have been delivered from a central lumen or passage of the scaffold into the aneurysmal space surrounding the scaffold. As an alternative, the expandable structures may also be delivered by positioning a delivery catheter on the outside of the scaffold, as illustrated generally in FIGS. 11A-11D. Usually, the delivery catheter 12 will be positioned so that the expandable structure 16 is located in the aneurysmal space AS prior to deployment of the scaffold 10. The expandable structure 16 may then be expanded or partially expanded before placement of the scaffold 10, but will more usually be expanded after the scaffold 10 has been fully expanded. As shown in FIG. 11A, a single delivery catheter is positioned to deliver a single expandable structure 16, where the expandable structure 16 is expanded after deployment of a single scaffold 10. As shown in FIG. 11B, a pair of expandable structures 16a and 16b delivered by delivery catheters 12a and 12b, respectively, are positioned prior to deployment of the single scaffold 10. Again, the expandable structure 16a and 16b will be expanded after expansion of the scaffold 10. The use of delivery catheters 12 for delivering single or pairs of expandable structures 16 may also be utilized with parallel scaffolds 22 and 24, as shown in FIG. 11C, and with bifurcated scaffolds 26 as shown in FIG. 11D. While delivery of only a single or pair of expandable structures 16 is illustrated, it will be appreciated that the delivery catheter 12, 12a, or 12b, could be utilized together with a separate inflation tube for delivering multiple expandable structures through the lumen of the delivery catheter which will remain in place. After the delivery of expandable structures is complete, the delivery catheters 12 may with drawn from the outside of the scaffold 12, 22, 24, or 26.

In all deployment protocols described thus far which employ open lattice or mesh scaffolds, it will be appreciated that expansion of the expandable structures within the aneurysmal space may displace fluid or materials present in the aneurysmal space into the lumen of the scaffold. This is advantageous since it reduces the risk of over pressurization of the aneurysmal sac.

Figure 12:
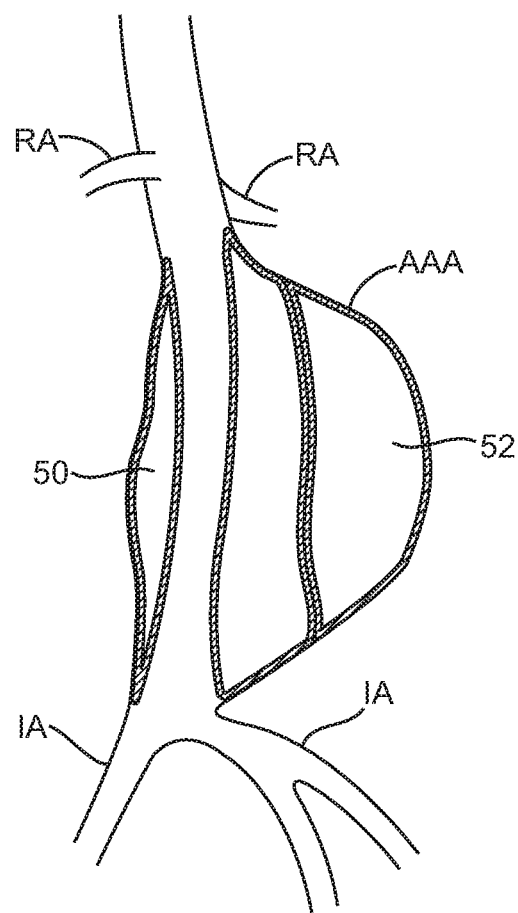
FIG. 12 illustrates use of an expandable structure for filling a void region around a double-walled fillable scaffold in accordance with the principles of the present invention.
Figure 13:
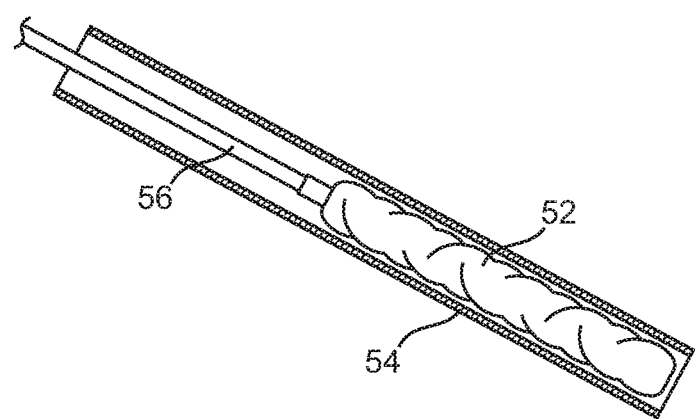
FIG. 13 illustrates a cannula which may be used for deploying an expandable structure percutaneously through an aneurysmal wall in accordance with the principles of the present invention.

Referring now to FIG. 12, use of the systems of the present invention for percutaneously accessing and filling a void in an aneurysmal sac after an earlier deployment of a scaffold in sealing system will be described. A double-walled filling structure 50 may be deployed within the abdominal aortic aneurysm AAA, generally as described in prior application Ser. No. 11/413,460, the full disclosure of which has been previously incorporated herein by reference. As the abdominal aortic aneurysm AAA shown in FIG. 12 is quite asymmetric, there may be sometimes be a void region left even after the filling structure 50 has been fully deployed. The present invention provides for percutaneous placement of an expandable structure 52 which is introduced through a penetration formed in the wall of the aneurysm. While shown in connection with the double-walled filling structure 50, it will be appreciated that such percutaneous introduction of expandable structures may be performed whenever there is a void left at the periphery of the aneurysmal space, or more commonly when such a void occurs sometime after an initial treatment of the aneurysm. The expandable structure 52 may be any of the inflatable or other members described previously, and will typically be introduced using a cannula 54 (FIG. 13) or other tubular introduction device. Cannula 54 carries the expandable structure 52 in a constrained configuration. The expandable structure 52 is connected to an inflation tube 56 or other device for delivering an expansion medium to the expandable structure. Penetration is formed in the wall of the aneurysm by conventional thoracoscopic or other techniques. Once the void is accessed, the cannula may be introduced through the penetration, and the expandable structure 52 advanced out a distal end of the cannula. After the expandable structure is in place, it may be inflated or otherwise expanded through inflation tube 56. After the expandable structure is fully expanded and/or the void is fully filled, the inflation member 56 may be detached and the expandable structure 52 sealed. Optionally, additional expandable structures may be introduced through the cannula until the entire void region is filled.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for treating an aneurysm in a blood vessel, said system comprising:
   a scaffold adapted to be placed in the aneurysm;
   a first fillable bag adapted to be expanded by filling a fillable space of the fillable bag with a non-fluid expansion medium to at least partly fill an aneurysmal space between an outside of the scaffold and an inside surface of the aneurysm; and
   a first delivery catheter adapted to:
      be positioned outside the scaffold,
      deliver the first fillable bag to the aneurysmal space between the outside of the scaffold and the inside surface of the aneurysm,
      deliver the expansion medium to fill the first fillable bag through the blood vessel when the fillable bag is positioned in the aneurysmal space, and
      detach the first fillable bag after expansion such that the expanded fillable bag remains within the aneurysmal space after removal of the catheter from the blood vessel;
   wherein the first fillable bag is configured to conform to the scaffold in the expanded state, and
   wherein the first fillable bag is configured to form a structure having a C-shaped cross-section when filled.

2. The system of claim 1, wherein said first fillable bag is configured to form and maintain the C-shaped cross-section when filled.

3. The system of claim 2, wherein said first fillable bag is configured to form a non-spherical structure when filled.

4. The system of claim 2, wherein the delivery catheter is adapted to be placed in the aneurysmal space after deployment of the scaffold.

5. The system of claim 2, wherein the fillable bag is adapted to be partially expanded before deployment of the scaffold.

6. The system of claim 2, wherein the fillable bag is adapted to be expanded after deployment of the scaffold.

7. The system of claim 2, further comprising a second delivery catheter adapted to:
 be positioned outside the scaffold,
 deliver a second fillable bag to the aneurysmal space between the outside of the scaffold and the inside surface of the aneurysm,
 deliver an expansion medium to the second fillable bag through the blood vessel when the fillable bag is positioned in the aneurysmal space, and
 detach the second fillable bag after expansion such that the expanded fillable bag remains within the aneurysmal space after removal of the catheter from the blood vessel.

8. The system of claim 7, wherein the second fillable bag is configured conform to the scaffold, the first fillable bag, or both, in the expanded state.

9. The system of claim 8, wherein the second delivery catheter is configured to deliver the second fillable bag to the aneurysmal space after the first fillable bag is expanded.

10. The system of claim 9, wherein the second delivery catheter is configured to deliver the second fillable bag to the aneurysmal space after the first fillable bag is detached inside the aneurysmal space.

11. The system of claim 7, wherein the second delivery catheter is configured to deliver the second fillable bag to the aneurysmal space concurrently with the first delivery catheter.

12. The system of claim 7, wherein the first and second fillable bags are not attached to each other.

13. The system of claim 12, wherein the first and second fillable bags are not attached to the scaffold.

14. The system of claim 2, wherein the first fillable bag comprises a channel for receiving the scaffold.

15. The system of claim 2, wherein the scaffold comprises an open lattice.

16. The system of claim 15 wherein the scaffold comprises a stent having a blood flow lumen.

17. The system of claim 15 wherein the scaffold comprises parallel stents.

18. The system of claim 15, wherein the scaffold comprises at least two distinct connected stents.

19. The system of claim 15 wherein the scaffold comprises a bifurcation.

20. The system of claim 2 wherein at least a portion of the scaffold comprises a stent graft.

21. A system for treating an aneurysm in a blood vessel, said system comprising:
 a scaffold adapted to be placed in the aneurysm;
 a first fillable bag adapted to be expanded by filling a fillable space of the fillable bag with a non-fluid expansion medium to at least partly fill an aneurysmal space between an outside of the scaffold and an inside surface of the aneurysm; and
 a first delivery catheter adapted to:
 be positioned outside the scaffold,
 deliver the first fillable bag to the aneurysmal space between the outside of the scaffold and the inside surface of the aneurysm,
 deliver the expansion medium to fill the first fillable bag through the blood vessel when the fillable bag is positioned in the aneurysmal space, and
 detach the first fillable bag after expansion such that the expanded fillable bag remains within the aneurysmal space after removal of the catheter from the blood vessel;
 wherein the first fillable bag is configured to form a structure having an axial channel along its entire axial length and a C-shaped cross-section when filled.

22. The system of claim 21, wherein the fillable bag forms an elongate structure.

* * * * *